(12) United States Patent
Zhu et al.

(10) Patent No.: US 6,363,281 B1
(45) Date of Patent: Mar. 26, 2002

(54) CARDIAC RHYTHM MANAGEMENT SYSTEM AND METHOD

(75) Inventors: Qingsheng Zhu, Little Canada; Avram Scheiner, Vadnais Heights, both of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/571,786

(22) Filed: May 16, 2000

(51) Int. Cl.[7] .................................................. A61N 1/37
(52) U.S. Cl. ............................................................. 607/28
(58) Field of Search ................................. 607/27, 28, 9, 607/5, 4

(56) References Cited

U.S. PATENT DOCUMENTS

| | | | |
|---|---|---|---|
| 5,324,310 A | 6/1994 | Greeninger et al. | 607/28 |
| 5,391,185 A | 2/1995 | Krool | 607/4 |
| 5,411,524 A | 5/1995 | Rahul | 607/4 |
| 5,683,429 A | 11/1997 | Mehra | 602/14 |
| 5,683,431 A | 11/1997 | Wang | 607/28 |
| 5,713,924 A | 2/1998 | Min et al. | 607/4 |
| 5,735,876 A | 4/1998 | Krool et al. | 607/5 |
| 5,797,967 A | 8/1998 | KenKnight | 607/4 |
| 5,799,350 A | 9/1998 | Ferek-Patric et al. | 607/17 |
| 5,800,465 A | 9/1998 | Thompson et al. | 607/9 |
| 5,814,079 A | 9/1998 | Kieval | 607/4 |
| 5,836,976 A | 11/1998 | Min et al. | 607/6 |
| 5,871,508 A | 2/1999 | Thompson et al. | 607/9 |
| 5,954,752 A | 9/1999 | Mongeon et al. | 607/6 |
| 5,999,850 A | 12/1999 | Dawson et al. | 607/4 |
| 6,070,100 A | 5/2000 | Bakels et al. | 607/9 |
| RE36,765 E | 7/2000 | Mehra | 607/4 |

*Primary Examiner*—Scott M. Getzow
(74) *Attorney, Agent, or Firm*—Schwegman, Lundberg, Woessner & Kluth, P.A.

(57) ABSTRACT

A system and method for cardiac rhythm management, which includes an electrode system having at least one electrode and control circuitry coupled to the electrode system from which a first cardiac signal is sensed. The control circuitry includes a pulse circuit to produce electrical pulses at a first value to be delivered to the electrode system in a first cardiac region. At least one cardiac signal is sensed from a second cardiac region, where the cardiac signal includes indications of cardiac depolarizations from the second cardiac region which occurs in direct reaction to the electrical pulses delivered to the first cardiac region. The first value of the electrical pulses are then modified by a pulse adjustment circuit when a cardiac depolarization which occurs in direct reaction to the electrical pulse delivered to the first cardiac region is detected from the second cardiac region.

37 Claims, 8 Drawing Sheets

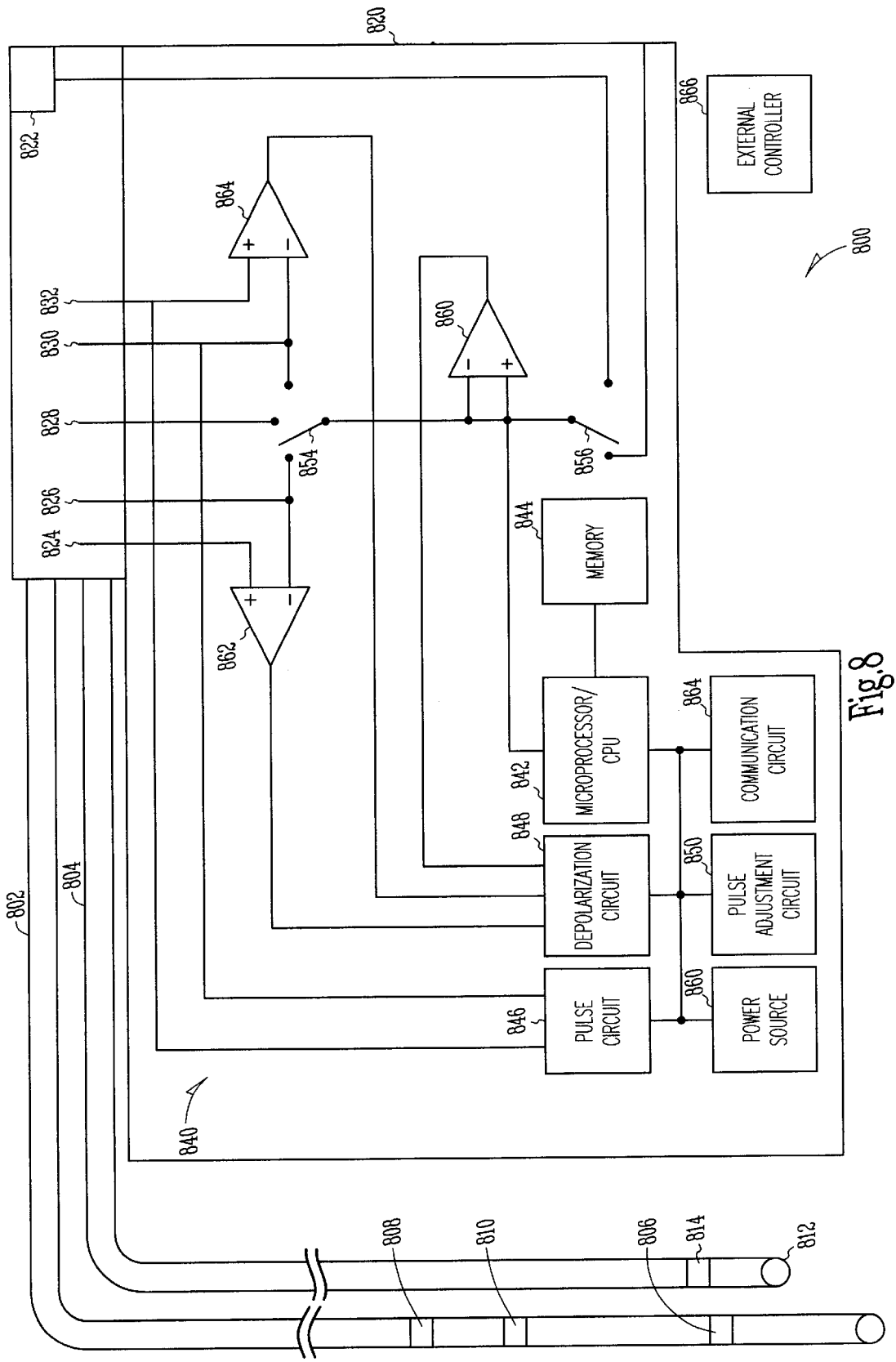

CARDIAC RHYTHM MANAGEMENT SYSTEM AND METHOD

FIELD OF THE INVENTION

This invention relates generally to the field of medical devices, and more particularly to an implantable cardiac rhythm management device which generates electrical pulses.

BACKGROUND

The heart is generally divided into four chambers, two atrial chambers and the two ventricular chambers. As the heart beats, the atrial chambers and the ventricular chambers of the heart go through a cardiac cycle. The cardiac cycle consists of one complete sequence of contraction and relaxation of the chambers of the heart.

The terms systole and diastole are used to describe the contraction and relaxation phases the chambers of the heart experience during a cardiac cycle. In systole, the ventricular muscle cells are contracting to pump blood through the circulatory system. During diastole, the ventricular muscle cells relax, causing blood from the atrial chambers to fill the ventricular chambers. After the period of diastolic filling, the systolic phase of a new cardiac cycle is initiated. Control over the timing and order of the atrial and ventricular contractions during the cardiac cycle is critical for the heart to pump blood efficiently. Efficient pumping action of the heart requires precise coordination of the contraction of individual cardiac muscle cells.

Implantable cardiac pacemakers have been successfully used to maintain control over the timing and order of the cardiac cycle. In its simplest form, the cardiac pacemaker is an electrical circuit in which a battery provides electricity that travels through a cardiac lead to a cardiac electrode and into the heart causing a contraction, and back to the battery to complete the circuit. Cardiac electrodes are typically implanted within or adjacent one cardiac chamber. This allows for cardiac signals to be sensed predominately from that chamber and for electrical energy pulses to be delivered to that chamber. For example, tip electrodes on transvenous leads are typically implanted in the apex of the right ventricular chamber or at or near the atrial appendage of the right atrium. Because the tip electrode is implanted completely within one cardiac chamber, electrical pulses provided through the tip electrode stimulate the chamber in which the electrode is implanted. So, for example, a pacing pulse delivered to an atrial electrode implanted in the atrial appendage stimulates the atria to contract. Likewise, a pacing pulse delivered to a ventricular electrode implanted in the right ventricle apex stimulates the ventricles to contract.

A current trend in cardiac rhythm management devices, also referred to as implantable pulse generator systems, is to implant cardiac electrodes in and/or through the coronary sinus vein. The coronary sinus vein drains venous blood from the coronary arteries into the right atrium. The coronary sinus vein also allows access to cardiac locations that are adjacent to either the left atrium and/or the left ventricle, where access to the left ventricle is typically gained through the great cardiac vein which is coupled to the coronary sinus vein. As such, the coronary sinus vein is an avenue for accessing, sensing and providing stimulation to different sites of the heart.

One difficulty encountered when using transvenous electrodes implanted within the coronary sinus is that electrical pulses delivered to capture the atrium can also capture the ventricles, or visa versa. This situation is referred to as "cross capture." Cross capture arises from the fact that the coronary sinus is generally located between the atrial chambers and the ventricular chambers along the anterior groove. When transvenous electrodes are positioned in this region of the heart it is possible for electrical pulses intended to stimulate the atrial chamber to instead, or in addition to, stimulate the ventricular chamber. This situation is undesirable, as hemodynamic efficiency is adversely effected when the ventricles contract too soon with respect to the atrial chambers. Thus, a need exists for a reliable way of preventing unintentional cross capture pacing.

SUMMARY OF THE INVENTION

The present subject matter provides a system and method to address the aforementioned problems. In one embodiment, the present subject matter utilizes autocapture protocols to monitor the capture of both atrium and ventricle chambers in response to electrical energy supplied to one or more electrodes positioned in or around the coronary sinus vein. Depending upon which chambers of the heart are captured, the present subject matter uses the information to adjust the energy level of pulses supplied to the one or more electrodes. Thus, the present subject matter can be used to prevent unintentional cross capture pacing (i.e., to prevent pulses intended to capture the atria from instead capturing the ventricles, and visa versa).

The present system provides for electrical pulses having a first value to be delivered to a first cardiac region. The system also senses at least one cardiac signal, where the cardiac signal includes indications of cardiac depolarizations resulting from the electrical pulses. In one embodiment, the system detects in the first cardiac signal cardiac depolarizations from a second cardiac region which occurs in direct reaction to an electrical pulse delivered to the first cardiac region. When one or more cardiac depolarizations occurring in direct reaction to electrical pulses delivered to the first cardiac region are detected in the second cardiac region the first value of the electrical pulses are modified so as to eliminate the depolarizations in the second cardiac region caused as a direct reaction to the electrical pulses.

In one embodiment, the first cardiac region is a supraventricular location and the second cardiac region is a ventricular cardiac region, so that the system delivers the electrical pulses to the supraventricular location and detects the cardiac signal from the ventricular cardiac region. Alternatively, the first cardiac region is the ventricular location and the second cardiac region is the supraventricular cardiac region, so that the system delivers the electrical pulses to the ventricular location and detects the cardiac signal from the supraventricular cardiac region.

In one embodiment, threshold test is used to set the first value of the electrical pulses. In one embodiment, test pacing pulses are delivered for the threshold test, where the values of the test pacing pulses are greater than a first value range and include an initial high-test pacing pulse. The cardiac signal is analyzed for cardiac depolarizations from the first cardiac region and the second cardiac region which occur as a result of the initial high-test pacing pulse. The values of the test pacing pulses are then reduced over the first value range until a second cardiac region pacing threshold value is reached where the second cardiac region is no longer depolarized and the first cardiac region is depolarized by the test pacing pulses. The values of the test pacing pulses continue to be reduced over the first value range until a first cardiac region pacing threshold value is reached where both the first cardiac region and the second cardiac region are no longer depolarized by the test pacing pulses. The first value of the pacing pulses is then set based on the first cardiac region pacing threshold value and the second cardiac region pacing threshold value.

In an alternative embodiment, the threshold test includes delivering test pacing pulses, including an initial low-test pacing pulse, at values over a first value range to the first cardiac region. The cardiac signal is then analyzed for cardiac depolarizations from the first cardiac region and the second cardiac region which occur as a result of the initial low-test pacing pulse. The values of the test pacing pulses are then increased over the first value range until a first cardiac region pacing threshold value is reached where the first cardiac region is depolarized and the second cardiac region is not depolarized by the test pacing pulses. The values of the test pacing pulses are continued to be increased over the first value range until a second cardiac region pacing threshold value is reached where both the first cardiac region and the second cardiac region are depolarized by the test pacing pulses. The first value is then set based on the first cardiac region pacing threshold value and the second cardiac region pacing threshold value.

These and other features and advantages of the invention will become apparent from the following description of the preferred embodiments of the invention.

BRIEF DESCRIPTION OF THE DRAWINGS

FIG. 8 is a block diagram of one embodiment of an implantable medical device according to the present subject matter.

DETAILED DESCRIPTION

Figure 1:
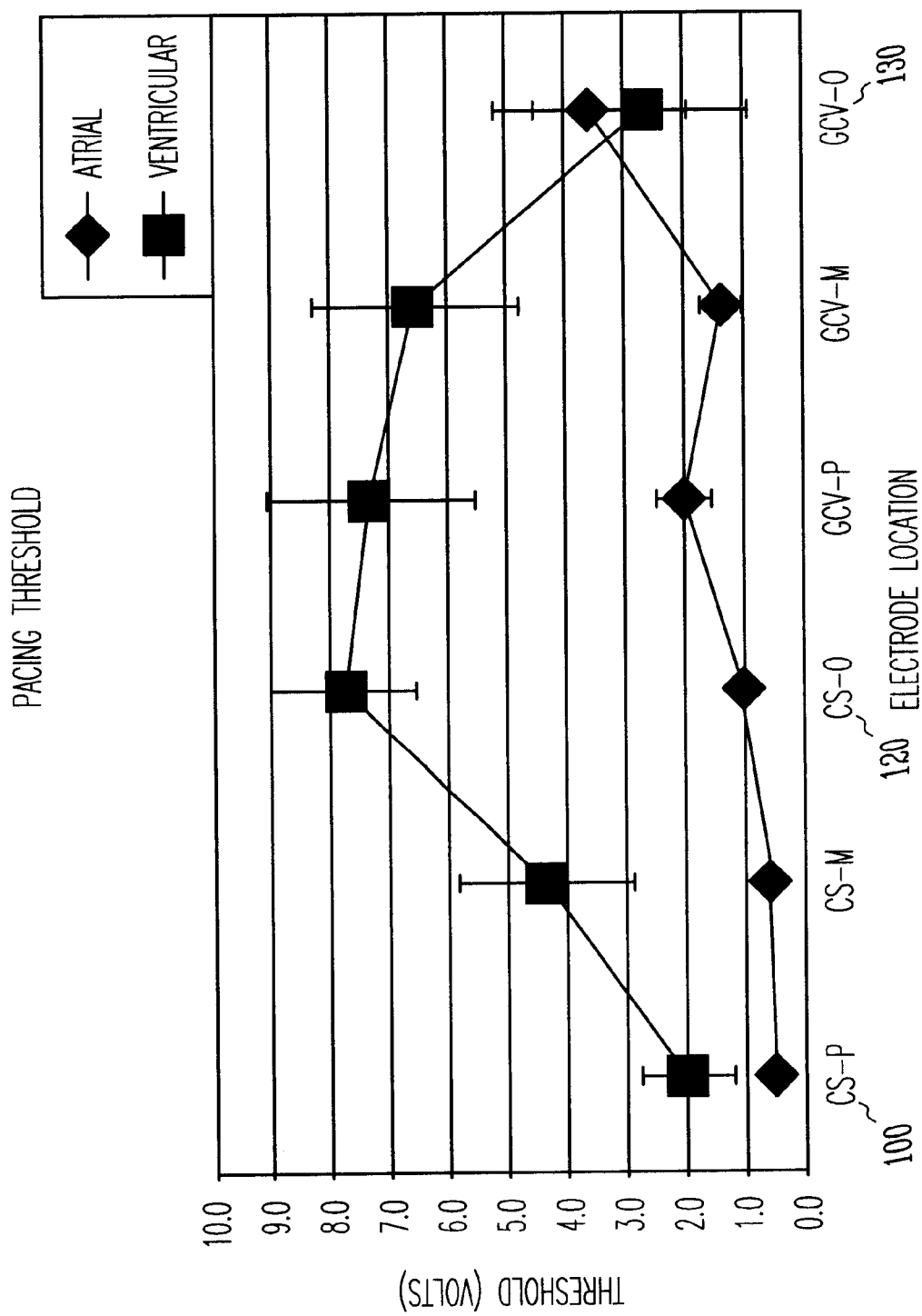
FIG. 1 is a graph of pacing threshold values versus electrode positions according to the present subject matter.

In the following detailed description, references are made to the accompanying drawings that illustrate specific embodiments in which the invention may be practiced. Electrical, mechanical, programmatic and structural changes may be made to the embodiments without departing from the spirit and scope of the present invention. The following detailed description is, therefore, not to be taken in a limiting sense and the scope of the present invention is defined by the appended claims and their equivalents.

Typically, transvenous electrodes are implanted within one cardiac chamber. This allows for cardiac signals to be sensed predominately from that chamber and for electrical energy pulses to be delivered to that chamber. For example, tip electrodes on transvenous leads are typically implanted in the apex of the right ventricular chamber or at or near the atrial appendage of the right atrium. Because the tip electrode is implanted completely within one cardiac chamber, electrical pulses provided through the tip electrode stimulate the chamber in which the electrode is implanted. So, for example, a pacing pulse delivered to an atrial electrode implanted in the atrial appendage stimulates the atria to contract. Likewise, a pacing pulse delivered to a ventricular electrode implanted in the right ventricle apex stimulates the ventricles to contract.

A current trend in cardiac rhythm management devices, also referred to as implantable pulse generator systems, is to implant cardiac electrodes in and/or through the coronary sinus vein. The coronary sinus vein drains venous blood from the coronary arteries into the right atrium. The coronary sinus vein also allows access to cardiac locations that are adjacent to either the left atrium and/or the left ventricle, where access to the left ventricle is typically gained through the great cardiac vein which is coupled to the coronary sinus vein. As such, the coronary sinus vein is an avenue for accessing, sensing and providing stimulation to different sites of the heart.

One difficulty encountered when using transvenous electrodes implanted within the coronary sinus is that electrical pulses delivered to capture the atrium can also capture the ventricles. This difficulty arises from the fact that the coronary sinus is generally located between the atrial chambers and the ventricular chambers along the anterior groove. When transvenous electrodes are positioned in this region of the heart it is possible for electrical pulses intended to stimulate the atrial chamber to instead, or in addition to, stimulate the ventricular chamber. This situation is undesirable, as hemodynamic efficiency is adversely effected when the ventricles contract too soon with respect to the atrial chambers.

The present subject matter provides a system and method to address the aforementioned problems. In one embodiment, the present subject matter utilizes autocapture protocols, described below, to monitor the capture of both atrium and ventricle chambers in response to electrical energy supplied to one or more electrodes positioned in or around the coronary sinus vein. Depending upon which chambers of the heart are captured, the present subject matter uses the information to adjust the energy level of pulses supplied to the one or more electrodes. Thus, the present subject matter can be used to prevent unintentional cross capture pacing (i.e., to prevent pulses intended to capture the atria from instead capturing the ventricles, and visa versa).

Referring now to FIG. 1, there is shown a graph of atrial and ventricular pacing thresholds as a function of electrode location within either the coronary sinus or the great cardiac vein. Each pair of data points represent the atrial and ventricular pacing threshold from proximal, middle and distal positions within the coronary sinus and the great coronary vein. In most locations, atrial capture threshold is lower than the ventricular threshold, where the difference varies with location of the electrode location.

Research data, such as shown in FIG. 1, shows that stimulation pulses from electrodes implanted in the coronary sinus vein or the great cardiac vein are capable of capturing both the atrium and the ventricles, depending upon the value of the pulses. For example, when the stimulation electrode was implanted in the proximal coronary sinus 100, the difference in values of the stimulation pulses required to capture the atrium and the ventricles was significantly smaller than the difference in values of the stimulation pulses required to capture the atrium and the ventricles when the stimulation electrode was implanted in the distal portion of the coronary sinus 120. At 130, when the electrode is implanted at a distal position in the great coronary vein, the data generally indicates that the atrial pacing threshold is greater than the ventricular pacing threshold.

These relative differences in pacing threshold of the atrium and ventricles are important considerations in ensuring the intended chamber of the heart is paced from positions within the coronary sinus and the great cardiac vein. Leads may migrate within the coronary sinus or the great cardiac vein, changing the initial location of the electrode and the threshold necessary to pace the intended chamber. In one embodiment, when the cardiac rhythm management device is programmed with a fixed pacing output for atrial pacing to one or more electrodes implanted in the coronary sinus, migration of the electrodes within the coronary sinus or the great cardiac vein may cause either loss of capture of the atrium with the pacing pulses, capture of the ventricles or both. Changes in pacing threshold due to changes in location of the electrodes within the coronary sinus can also be exacerbated by changes in threshold voltage that occur as the lead matures. Thus, over time the fixed pacing output for atrial pacing from the coronary sinus and/or the great cardiac vein can fail to be sufficient to capture the atria and/or begin to capture the ventricles. The present subject matter addresses these issues.

Figure 2:
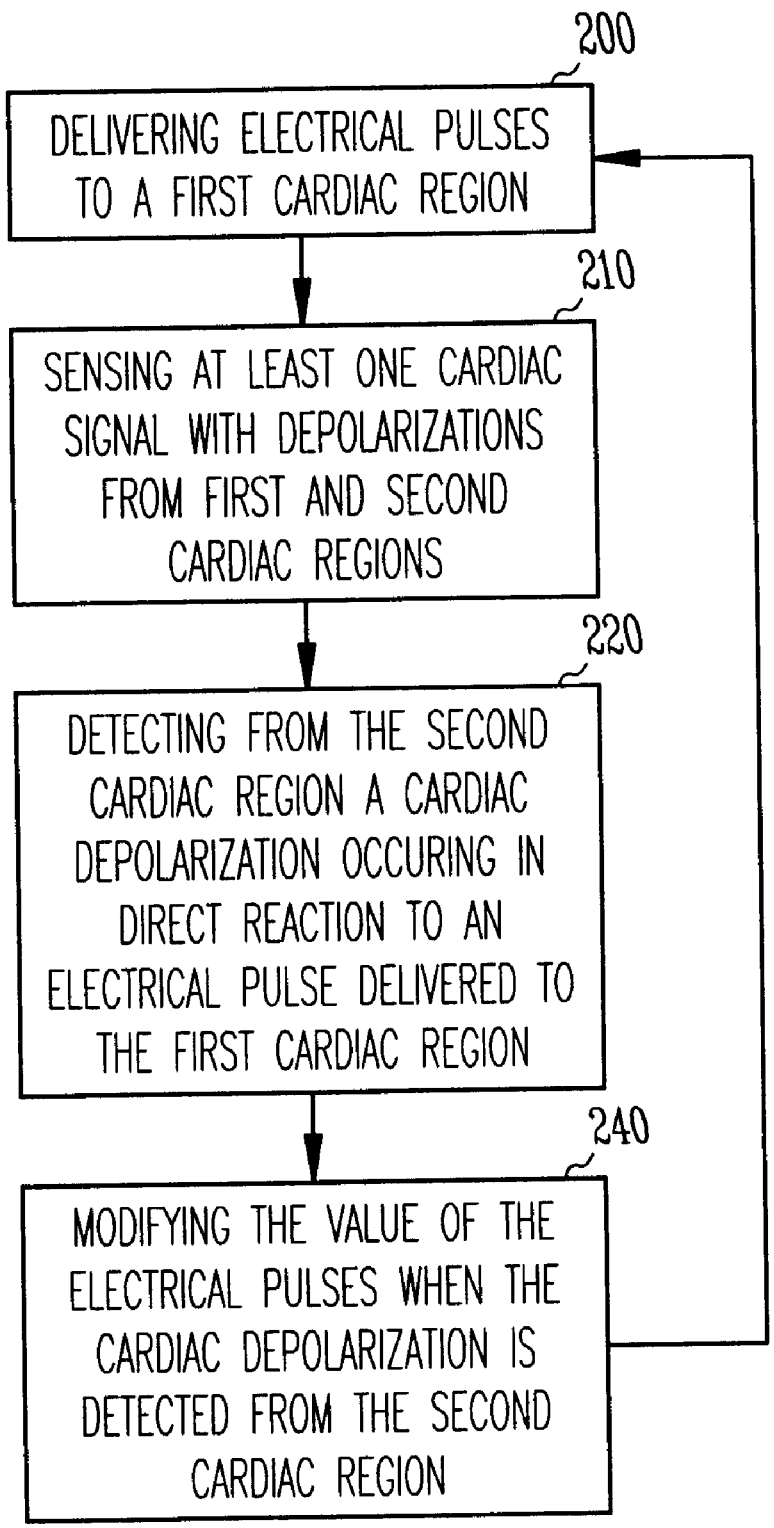
FIG. 2 is a flow chart illustrating one embodiment of the present subject matter.

Referring now to FIG. 2, there is shown one embodiment of a method for the present subject matter. At 200, electrical pulses having a first value are delivered to a first cardiac region. In one embodiment, the first value of the electrical pulses is a voltage value which is useful in capturing one or more cardiac chambers (e.g., atrial chambers or ventricular chambers). Alternatively, the first value is a width of an electrical pulse which is useful in capturing one or more cardiac chambers (e.g., atrial chambers or ventricular chambers). By way of example, and not by way of limitation, the electrical pulses used in the present subject matter are pacing level pulses. In one embodiment, the first value of the pacing level pulses are voltages in the range of 0.1 to 10 volts. Alternatively, the first value for the pacing level pulses are pacing pulses having a pulse width in the range of 0.1 to 20 milliseconds.

In addition to delivering electrical pulses to the first cardiac region, at least one cardiac signal is also sensed at 210, where the cardiac signal includes indications of cardiac depolarizations from the first cardiac region and/or from a second cardiac region. In one embodiment, the cardiac signals are either unipolar signals sensed between an electrode implanted in the heart and the housing of the cardiac rhythm management device or an indifferent electrode mounted on or near the cardiac rhythm management device. Alternatively, the sensed signal is a bipolar signal sensed between two electrodes implanted within the heart.

At 220, the cardiac signal containing indications of cardiac depolarizations from the second cardiac region is analyzed to detect a cardiac depolarization that occurs as a direct reaction to an electrical pulse delivered to the first cardiac region. In one embodiment, a cardiac depolarization occurring in the second cardiac region as a direct reaction to a pulse delivered to the first cardiac region is identified based on the short time duration between the delivery of the pulse and the occurrence of the depolarization in the second cardiac region (e.g., a time duration shorter than AV-delay). Alternatively, autocapture systems and/or methods may be employed to identify cardiac depolarizations occurring as a direct result of delivered pacing pulses.

Autocapture systems and/or methods have been suggested as a way of identifying evoked responses from sensed cardiac signals. One problem faced by such systems is dealing with "afterpotential", or polarization voltage. Typically, an "afterpotential", or polarization voltage, develops in the cardiac tissue surrounding a pacing/sensing electrode after the electrode is used to deliver a pacing pulse. The afterpotential typically has a voltage and a duration that is so large that any response of the cardiac tissue evoked by the pacing pulse is masked or buried within the afterpotential. This is an undesirable result as verification of capture by an implantable pulse generator is hampered.

One example of an autocapture system and method for identifying evoked depolarizations is where an "afterpotential", or polarization voltage, resulting from a pacing pulse is attenuated to allow for the evoked response to be readily identified. In one embodiment, attenuation of the afterpotential is accomplished with an improved pacing output circuit which is the subject matter of a co-pending U.S. patent application entitled "Improved Pacing Output Coupling Capacitor for Automatic Capture Threshold Detection In Cardiac Pacing Systems", where the co-pending application is a Continuation-in-part application of application Ser. No. 08/977,272, filed Nov. 24, 1997, entitled "Pacing Output Circuitry For Automatic Capture Threshold Detection In Cardiac Pacing Systems", where all of the co-pending applications are hereby incorporated by reference in their entirety.

Figure 3:
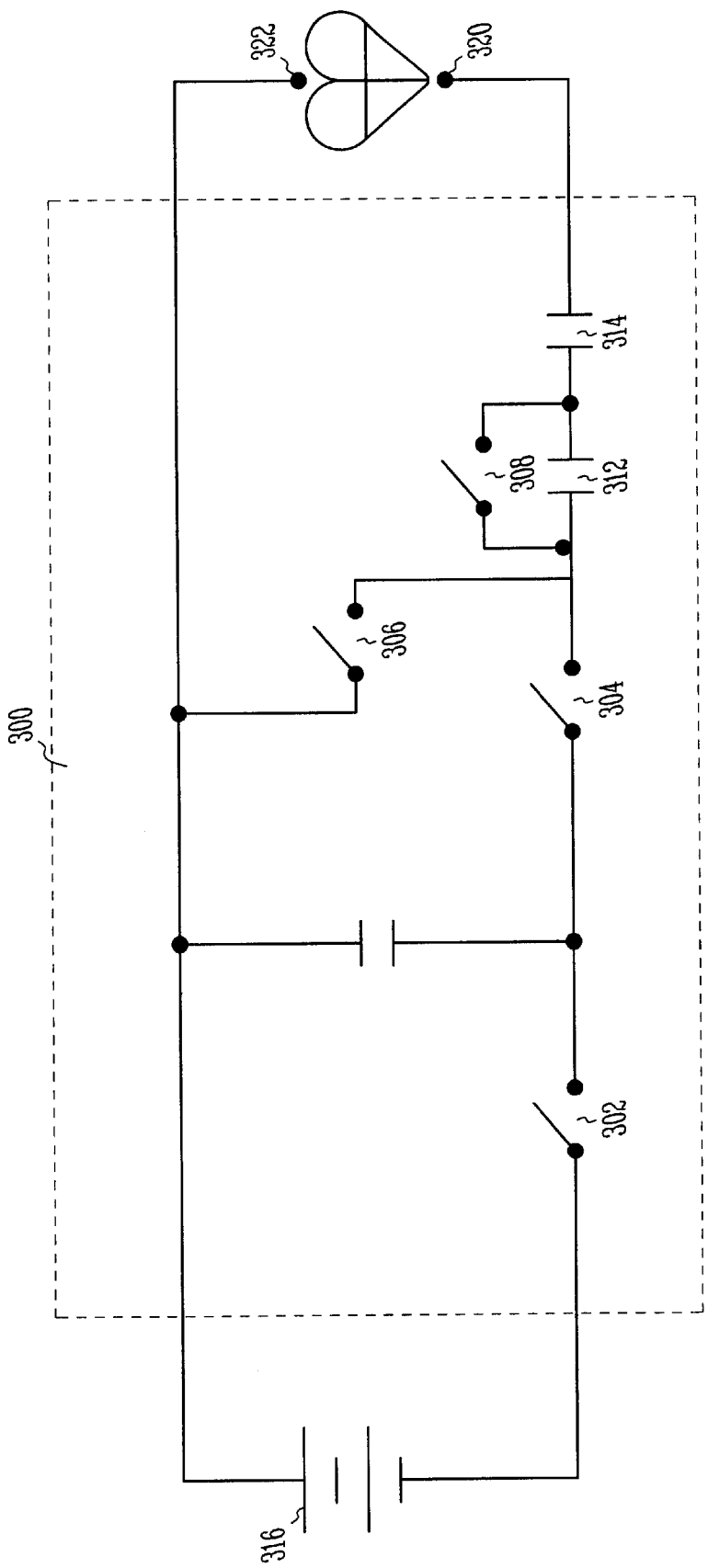
FIG. 3 is a schematic diagram according to one embodiment of the present subject matter.

Referring now to FIG. 3, there is shown one embodiment of the pacing output circuit 300. The pacing output circuit 300 is shown having switches 302, 304, 306, 308, a pacing charge capacitor 310, a first coupling capacitor 312, and a second coupling capacitor 314, where the circuit 300 is coupled to a power supply 316 and to sensing and pacing electrodes 320 and 322. In one embodiment, sensing and pacing electrodes 320 and 322 can have any number of configurations, including but not limited to ring and/or tip electrodes. Additionally, the pacing charge capacitor 310 can have a capacitance suitable for use in a pulse generator, where a capacitance of greater than 10 microfarads is possible. The circuit 300 can be integrated into a cardiac rhythm management system, including, but not limited to, pacemakers and implantable cardioverter/defibrillators.

In the pacing output circuit 300, one function of the second coupling capacitor 314 is to block DC signals from reaching a heart during pacing. Additionally, the second coupling capacitor 314 has a sufficiently large capacitance in order to minimize pacing pulse droop. In one embodiment, the second coupling capacitor 314 has a capacitance of greater than 10 microfarads. In an additional embodiment, the first coupling capacitor 312 has a capacitance that is less than the second coupling capacitor 314. In one embodiment, the first coupling capacitor 312 has a capacitance of less than 5 microfarads. The first coupling capacitor 312 is selectively employed, via switch 308 to selectively reduce the effective capacitance of the second coupling capacitor 314, thereby quickly attenuating the polarization voltage or "afterpotential" resulting from pacing delivered between electrodes 320 and 322.

In operation, the pacing output circuit 300 performs a charging cycle, a pacing cycle and a recharge cycle. During the charging cycle, switch 302 is closed and switches 304–308 are open to charge capacitor 310. During the pacing cycle, energy for pacing is supplied from the capacitor 310 by opening switches 302 and 306 and closing switches 304 and 308. Voltage is then discharged through the second coupling capacitor 314 to the electrodes 320 and 322.

By bypassing the first coupling capacitor 312, the second coupling capacitor 96 is at its full capacitance level. This serves to effectively block DC signals from reaching the heart. During the recharging cycle, switches 302 and 304 are open and switch 306 is closed. This allows the circuit 300 to passively recharge as the charge within the heart flows back into the circuit 300 to balance out. During this passive recharge period, the charge on the second coupling capacitor 314 may be such that the afterpotential signal exponentially decays over a relatively long period of time (e.g., lasting up to 100 milliseconds). This large "afterpotential" signal masks any evoked response of the heart from the pacing pulse. This is because the evoked response from the heart typically occurs within 20 milliseconds from delivery of the stimulus pulse and are smaller in magnitude than the large "afterpotential" which would develop within the second coupling capacitor 314 if it were not attenuated. Attenuation of the afterpotential is achieved by having the switch 308 in the open state such that the first coupling capacitor 312 and second coupling capacitor 314 are connected in series. Series coupling of capacitors 312 and 314 causes the overall capacitance to approximate the lower capacitance (i.e., the capacitance of the first capacitor 312). This lower effective capacitance quickly attenuates the polarization voltage or "afterpotentials" which results immediately following the application of a stimulation pulse such that the evoked response of the heart will not be buried or masked within the afterpotential. This in turn allows for the identification of an evoked response (or capture) of the heart.

Referring again to FIG. 2, at 240, when the cardiac depolarization detected from the second cardiac region is identified as occurring in direct reaction to the electrical pulse delivered to the first cardiac region in 220, the first value of the electrical pulses is modified. In one embodiment, the first value of the electrical pulses is lowered by a first amount when the cardiac depolarization in the second cardiac region occurs in direct reaction to the electrical pulse delivered to the first cardiac region. Alternatively, the first value of the electrical pulses is lowed by a first percentage of the voltage value. In one embodiment, the value of the electrical pulses is lowered by approximately two tenths (0.2) volts. Alternatively, the first percentage of the voltage value is in a range of approximately 5 to 20 percent.

Figure 4:
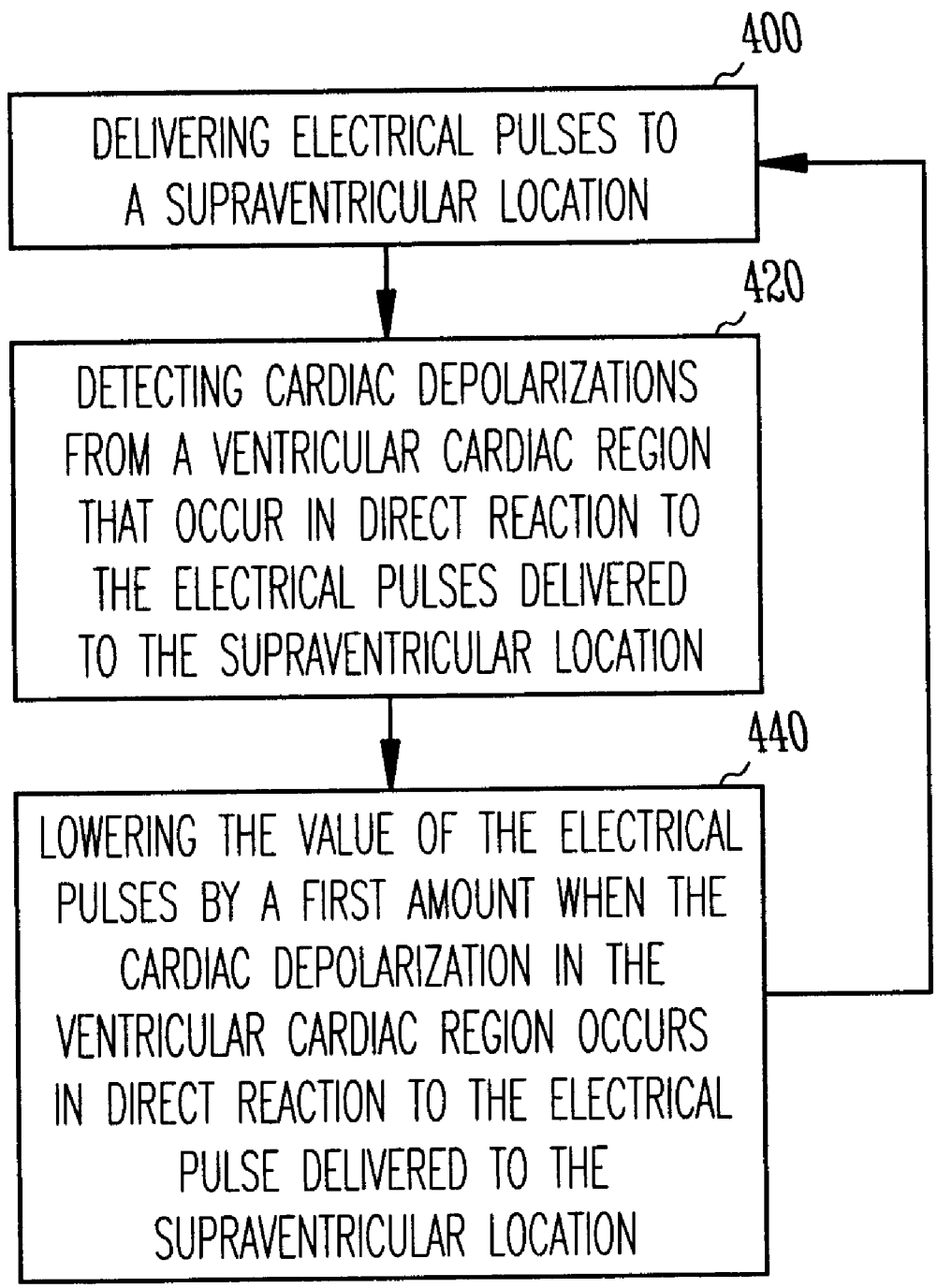
FIG. 4 is a flow chart illustrating one embodiment of the present subject matter.

Referring now to FIG. 4, there is shown an additional embodiment of the method for the present subject matter. For the embodiment of FIG. 4, the first cardiac region is a supraventricular location of the heart, from which an atrial cardiac signal is sensed. By way of example, and not by way of limitation, the supraventricular location includes a location within the coronary sinus vein, where the atrial cardiac signal contains indications of atrial contraction events. Additionally, the second cardiac region is a ventricular region of the heart, where the one or more electrodes located within the supraventricular location are used to sense cardiac activity from the second cardiac region (e.g., the ventricular region of the heart). Alternatively, additional electrodes are implanted either in a right ventricle location or a location adjacent the left ventricle of the heart, accessed through the coronary sinus/great cardiac vein, from which a ventricular cardiac signal is sensed. The ventricular cardiac signal contains indications of ventricular contraction events which are then used in the present subject matter. In an alternative embodiment, the labels given to the cardiac signals sensed from the atrial and ventricular regions of the heart can be reversed for the present subject matter, such that the first cardiac region is the ventricular region of the heart as described, while the second cardiac region is the atrial region of the heart, as described.

At 400, electrical pulses having a first value are delivered to the supraventricular location. In one embodiment, the first value of the electrical pulses is the first voltage value as previously described. Alternatively, the first value is the width of an electrical pulse, as previously described. At 420, a cardiac signal is sensed and analyzed to detect indications of cardiac depolarizations from the ventricular cardiac region that occur as a direct reaction to the electrical pulse delivered to the supraventricular location. In one embodiment, the cardiac depolarization occurring in the ventricular region as a direct reaction to a pulse delivered to the supraventricular region is identified as previously described. At 440, when the cardiac depolarization detected from the ventricular cardiac region is identified as occurring in direct reaction to the electrical pulse delivered to the supraventricular region, the first value of the electrical pulses is modified. In one embodiment, the first value of the electrical pulses is lowered by a first amount or percentage, as previously described, when the cardiac depolarization in the ventricular cardiac region occurs in direct reaction to the electrical pulse delivered to the supraventricular cardiac region.

Referring now to FIG. 4, there is shown one embodiment for determining the first value of the electrical pulses delivered to the first cardiac region. In one embodiment, the process tests the threshold voltage required to capture the atria and the threshold voltage required to capture the ventricles. An average voltage of these two threshold voltages is then used as the first value of the electrical pulses delivered to the first cardiac region.

By way of example, and not by way of limitation, the process of testing the threshold voltages, or pulse widths, required to capture the atria and the ventricles can be accomplished with either a "step-up" or a "step-down" pacing protocol. The testing of the atria and ventricular thresholds is conducted at a first time interval. In one embodiment, the threshold testing is programmed to occur at any time from an hourly basis to a daily basis. Alternatively, other indicators/sensors from the cardiac rhythm management system can be used to trigger the threshold testing. For example, when beat-to-beat atrial autocapture is available.

Figure 5:
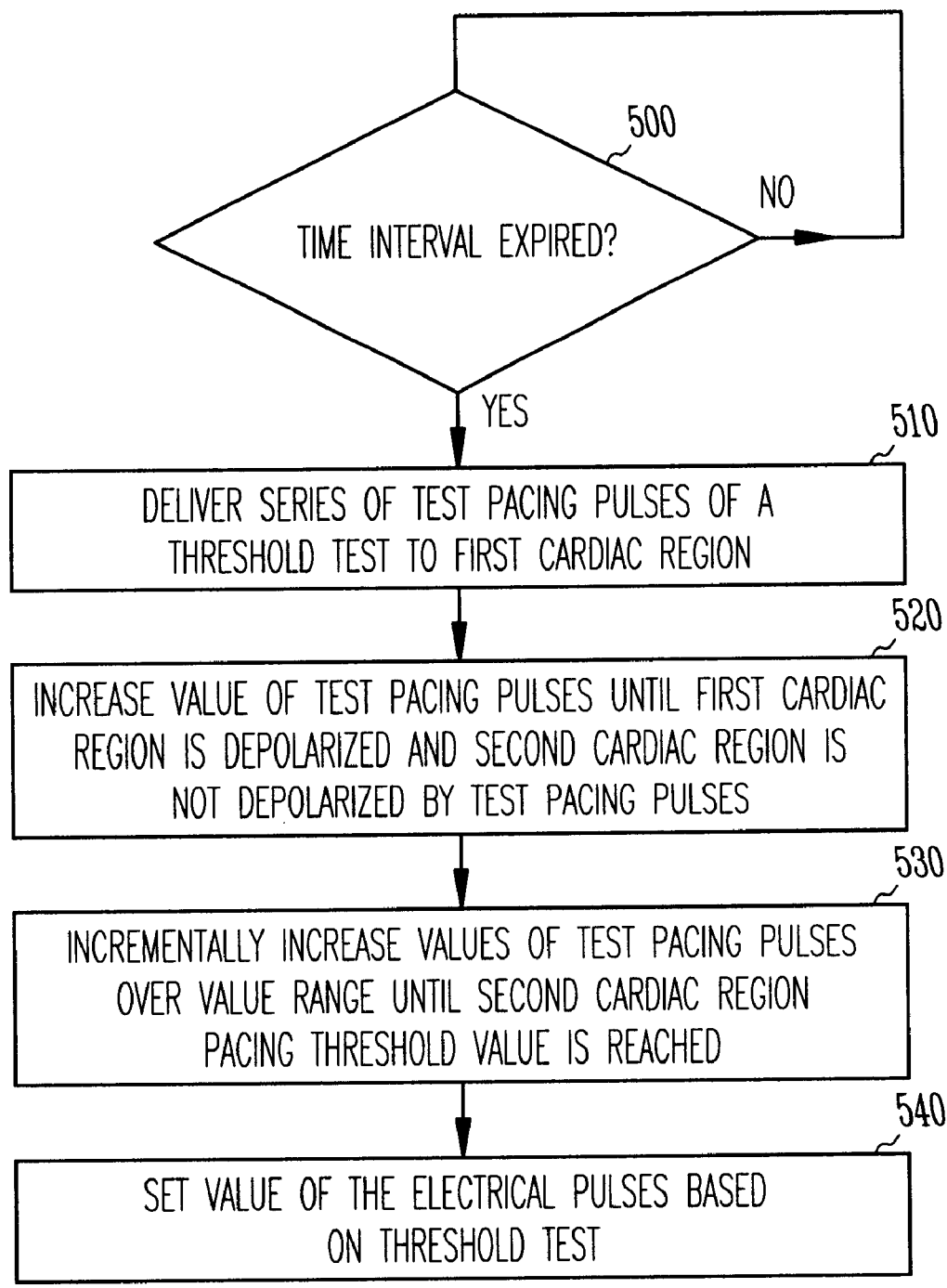
FIG. 5 is a flow chart illustrating one embodiment of the present subject matter.

FIG. 5 shows one example of a threshold test employing a step-up procedure. At 500, the first time interval is tested to determine if it has expired. When the first time interval has not expired, the system returns to 500 to make the next inquiry. When the first time interval has expired, however, the test moves to 510. At 510, a series of test pacing pulses are delivered to the first cardiac region, where each pacing pulse in test pacing pulses are delivered at a first value which varies over a first value range. In one embodiment, the first value range is a programmable range, where one range which can be used is from about 1 volt to 10 volts.

Initially, one or more pacing pulses of the test pacing pulses are delivered at an initial low-test pacing pulse, where the initial low-test pacing pulse is the pacing pulse with the lowest value in the first value range (e.g., has the lowest voltage value of the pacing pulses in the first value range). As the pacing pulse is delivered, the one or more cardiac signals are analyzed to detect the occurrence of cardiac depolarizations from the first cardiac region and/or the second cardiac region as a result of the pacing pulse (e.g., the initial low-test pacing pulse).

In one embodiment, the initial low-test pacing pulses will not cause either the first or second cardiac region to depolarize. At 520, the first value of the test pacing pulses is then increased incrementally over the first value range until the first cardiac region is depolarized and the second cardiac region is not depolarized by the test pacing pulses. The first value of the pacing pulse which causes this to happen is referred to as a first cardiac region pacing threshold value. At 530, the values of the test pacing pulses are then incrementally increased over the first value range until a second cardiac region pacing threshold value is reached. At this point, both the first cardiac region and the second cardiac region are depolarized by the test pacing pulses. In one embodiment, the incremental increase of the test pacing pulse is a programmable value in the range of 0.1 to 0.5 volts.

The first value of the electrical pulses to be delivered to the first cardiac region are then set based on the threshold test at 540. In one embodiment, the value of the electrical pulses to be delivered to the first cardiac region are set to a value that is based on the first and second cardiac region pacing threshold values. For example, the first value of the electrical pulses is set to a value that is between the first cardiac region pacing threshold value and the second cardiac region pacing threshold value. By way of further example, the first value of the pulses could be set to a value that is midway (an average or median value) between the first and second cardiac region pacing threshold values.

In an additional embodiment, a safety margin value is added to the first value calculated from the first and second cardiac region pacing threshold values. The safety margin accommodates for variations or changes in the pacing threshold of the first cardiac region. In one embodiment, the safety margin value is an additional amount of, for example, voltage or pulse width which is added to the first value calculated from the first and second cardiac region pacing threshold values. For example, the safety margin is a programmable value in the range of 0.1 to 0.8 volts, where 0.5 volts is one value that can be used. In an alternative embodiment, the safety margin is a first percentage of the calculated first value, where the first percentage is set in a range from 8 to 20 percent (%), where 20 percent is one value that can be used.

As discussed above, once the first value for the electrical pulse delivered to the first cardiac region is set, the at least one cardiac signal is monitored to detect the occurrence of a cardiac depolarization in the second cardiac region that is in direct reaction to the electrical pulse delivered to the first cardiac region. When an electrical pulse is determined to have caused a cardiac depolarization in the second cardiac region, the first value (e.g., voltage, pulse width) of the electrical pulse is lowered, as previously described, until cardiac depolarizations in the second cardiac region occurring in direct reaction to the electrical pulse are no longer detected. Once this occurs, the system will proceed to use this value of the electrical pulse until the sensed cardiac signals indicate the value needs to be changed. In an additional embodiment, if a situation develops where the first value of the electrical pulses drops to the point where the first cardiac region is not being captured by the electrical pulses delivered, but the second cardiac region continues to be captured by the electrical pulses, the protocol of the present subject matter discontinues delivering the electrical pulses to the first cardiac region.

Figure 6:
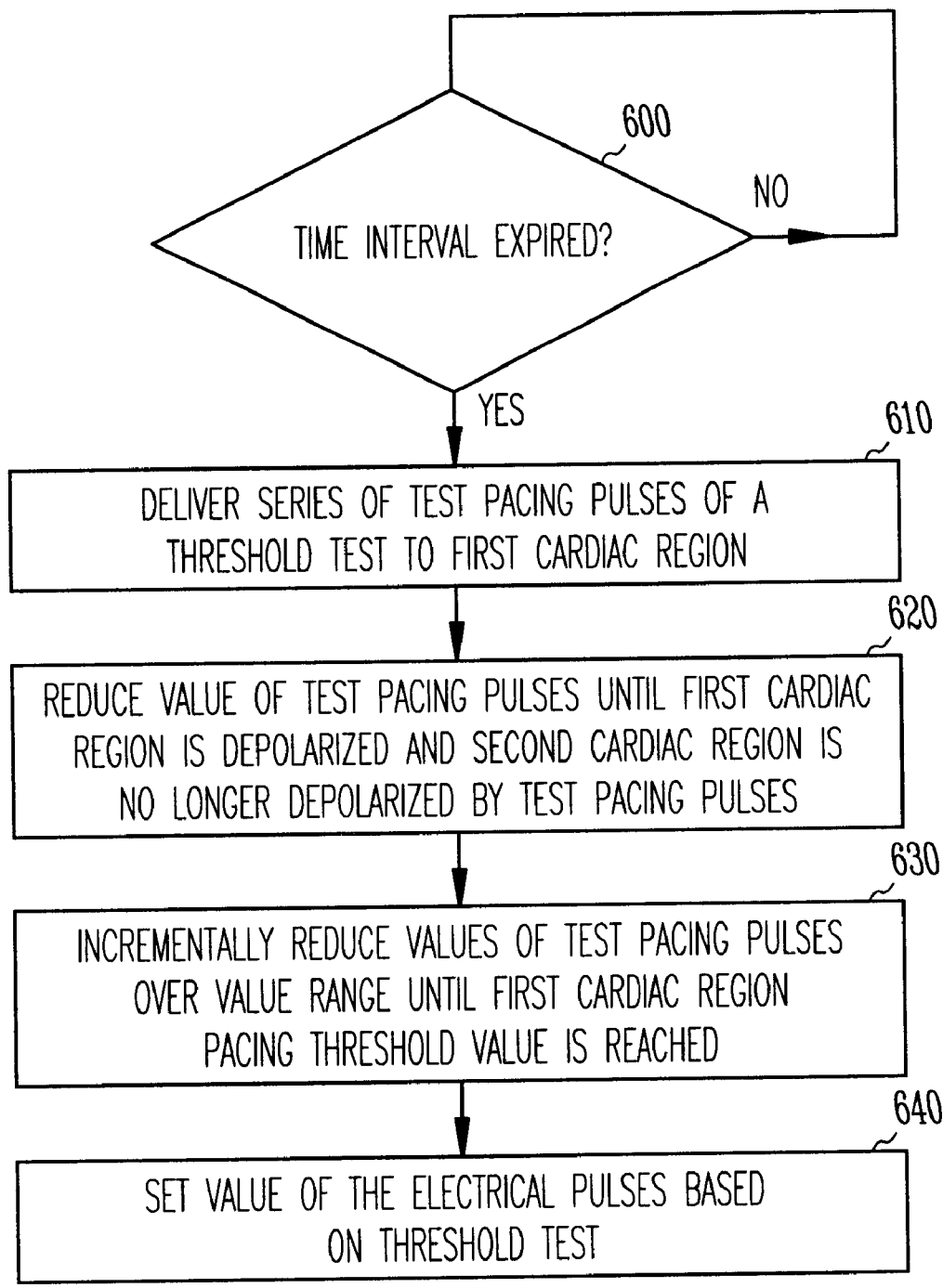
FIG. 6 is a flow chart illustrating one embodiment of the present subject matter.

Referring now to FIG. 6, there is shown one example of the threshold test employing a step-down procedure. At 600, the first time interval is tested to determine if it has expired. When the first time interval has not expired, the system returns to 600 to make the next inquiry. When the first time interval has expired, however, the test moves to 610. At 610, a series of test pacing pulses are delivered to the first cardiac region, where each pacing pulse in test pacing pulses are delivered at a first value which varies over a first value range. Initially, one or more pacing pulses of the test pacing pulses are delivered at an initial high-test pacing pulse, where the initial high-test pacing pulse is the pacing pulse with the highest value in the first value range (e.g., has the highest voltage value of the pacing pulses in the first value range). As the pacing pulse is delivered, the one or more cardiac signals are analyzed to detect the occurrence of cardiac depolarizations from the first cardiac region and/or the second cardiac region as a result of the pacing pulse (e.g., the initial high-test pacing pulse).

In one embodiment, the initial high-test pacing pulses causes both the first or second cardiac region to depolarize. At 620, the value of the test pacing pulses is then reduced incrementally over the first value range until the first cardiac region is depolarized, but the second cardiac region is no longer depolarized by the test pacing pulses. The value of the pacing pulse which causes this to happen is referred to as a second cardiac region pacing threshold value. At 630, the values of the test pacing pulses are then incrementally reduced over the first value range until a first cardiac region pacing threshold value is reached where both the first cardiac region and the second cardiac region are no longer depolarized by the test pacing pulses. The first value of the electrical pulses to be delivered to the first cardiac region are then set based on the threshold test at 640, as previously discussed for the threshold test employing a step-up procedure.

The present subject matter is useful for cardiac rhythm management systems having electrodes located in or around the atria, including electrodes located in the coronary sinus vein and/or the great coronary vein for the purpose of pacing the atrium.

The present subject matter can also be used with system which also have electrodes located in the ventricles and systems which use autocapture algorithms to detect and identify cardiac depolarizations in the atrium and the ventricles.

Figure 7:
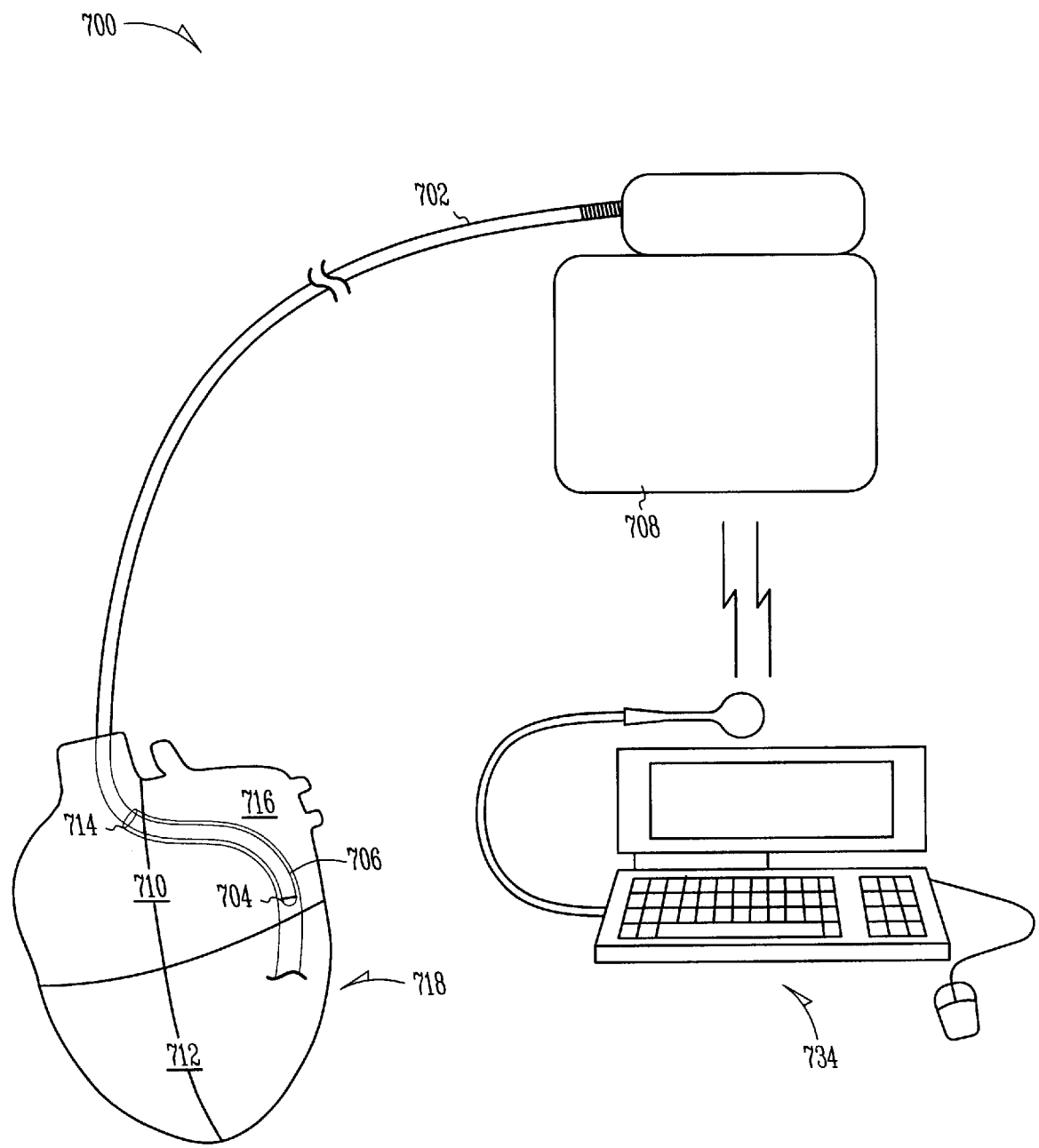
FIG. 7 is a schematic view of one embodiment of an implantable medical device according to one embodiment of the present subject matter.

Referring now to FIG. 7, there is shown a schematic of a cardiac rhythm management system 700 according to the present subject matter. In the present embodiment, the cardiac rhythm management system 700 includes an electrode system which includes a first cardiac lead 702 having at least one electrode 704. In one embodiment, the electrode 704 is a pace/sense electrode located at or near a distal end 706 of the first cardiac lead, where the electrode 704 is used to sense either unipolar cardiac signals (electrode and housing 708 of the system 700) or bipolar cardiac signals (when an additional electrode is in proximity to electrode 704). In one embodiment, the cardiac rhythm management system 700 includes control circuitry coupled to the at least one electrode 704 from which a first cardiac signal is sensed and from which the present subject matter is performed.

In the embodiment of FIG. 7, the first cardiac region is an atrial region 710 and the second cardiac region is a ventricular region 712. The first cardiac lead 702 is shown implanted in the supraventricular region of the heart, where the distal tip of the lead 702 is positioned in the coronary sinus vein 714. In one embodiment, the electrode 704 at the distal tip of lead 706 is positioned adjacent the left atrium 716 of the heart 718. From this location, the unipolar signal sensed between the electrode 704 and the housing 708 will contain indications of cardiac depolarizations (e.g., P-waves) from the atrium and cardiac depolarizations that occur in the ventricles (e.g., R-waves or QRS-complexes). In one embodiment, the electrode 704 is implanted in the coronary sinus 714 to provide for sensing and pacing to the atria and sensing from the ventricle. In this embodiment, the first cardiac region is the atria of the heart, while the second cardiac region is the ventricles of the heart. In an alternative embodiment, the electrode 704 is implanted in the coronary sinus 714 to provide for sensing and pacing to the ventricles (e.g., from a position adjacent the left ventricle) and sensing from the atrium. In this embodiment, the first cardiac region is the ventricles of the heart, while the second cardiac region is the atria of the heart.

In addition to providing electrode 704, additional electrodes can be positioned on the first cardiac lead 702. For example, one or more additional pacing/sensing electrodes and/or defibrillation coil electrodes can be located on the first cardiac lead to allow for any combination of unipolar and/or bipolar sensing between the electrode 704 and the additional electrode(s). Use of these additional electrodes then provides for a variety of possible sensing and shocking (e.g., pacing pulses) vectors between the electrodes themselves and/or the housing 708 of the cardiac rhythm management system 700. In an additional embodiment, the electrode system further includes a second cardiac lead, where the second cardiac lead includes one or more electrodes (pace/sense electrodes and/or defibrillation electrodes) and is implanted with one or more of the electrodes located in the right ventricular chamber to allow for cardiac depolarizations from the ventricles to be detected. Additionally, the first cardiac lead 702 can be of a length to allow the distal end 706 of the lead to be positioned adjacent the left ventricle (e.g., via the great cardiac vein) with the electrode 704 positioned on the lead body to allow the electrode 704 to be positioned between the left atrium 716 and the left ventricle (same relative position as shown in FIG. 7) and one or more additional electrodes positioned at or near the distal end 706 so as to place the additional electrodes adjacent the left ventricle.

FIG. 7 also shows a medical device programmer 734. The medical device programmer 734 and the cardiac rhythm management system 700 include communication circuitry which allows for cardiac data to be to and from the cardiac rhythm management system 700. In addition, command signals for controlling the operation of the cardiac rhythm management system 700 can also be sent between the medical device programmer 734 and the cardiac rhythm management system 700. In one embodiment, communication between the medical device programmer 734 and the cardiac rhythm management system 700 is established over a radio frequency telemetry channel, as is known in the art.

Referring now to FIG. 8, there is shown one embodiment of a cardiac rhythm management system according to the present subject matter. The system includes an implantable cardiac rhythm management device 800, a first cardiac lead 802 and a second cardiac lead 804. In one embodiment, both the first cardiac lead 802 and the second cardiac lead 804 include at least one electrode each. In the embodiment shown in FIG. 8, the first cardiac lead 802 includes a first ventricular electrode 806, a first atrial electrode 808 and a second atrial electrode 810. The second cardiac lead 804 is shown including a first ventricular electrode 812 and a second ventricular electrode 814.

FIG. 8 shows an embodiment in which the first ventricular electrode 806, the first atrial electrode 808 and the second atrial electrode 810 of the first cardiac lead 802 are ring electrodes (either partially or completely encircling the peripheral surface of the cardiac lead). FIG. 8 also shows the first ventricular electrode 712 being located at the distal end/tip of the second cardiac lead 804 and the second ventricular electrode 814 being a ring electrode (either partially or completely encircling the peripheral surface of the cardiac lead). However, additional electrode structures could be used, and are considered within the scope of the present invention.

In one embodiment, the first cardiac lead 802 is implanted within the heart, where the distal end of the lead 802 is implanted through the coronary sinus vein and the great cardiac vein to allow the first ventricular electrode 806 to be positioned adjacent the left ventricular chamber of the heart. In one embodiment, the first ventricular electrode 806 is used in conjunction with the housing 820 and/or an indifferent electrode 822 mounted on the implantable cardiac rhythm management device 800 to sensed, or detect, a cardiac signal (near field signal) from the heart. In addition, when implanted the first atrial electrode 808 and the second atrial electrode 810 are positioned in supraventricular region within the coronary sinus. In one embodiment, the first and second atrial electrodes, 808 and 810, are used to sense, or detect, a cardiac rate signal (near field signal) from the heart. Additionally, the second cardiac lead 804 is implanted within the heart, where the distal end of the lead 804 is implanted at the apex of the right ventricle to allow the first ventricular electrode 812 and the second ventricular electrode 814 to be implanted within the right ventricular chamber of the heart. In one embodiment, the first and second ventricular electrodes, 812 and 814, are used to sensed, or detect, a cardiac rate signal (near field signal) from the heart.

The electrodes are connected to electronic circuitry within the implantable cardiac rhythm management device 800 through lead conductors housed and electrically insulated within the body of the first and second cardiac leads 802 and 804. The lead conductors are coupled to lead connectors on the cardiac leads, which allow for the electrodes positioned on the leads to be coupled to the electronic circuitry through input terminals 824, 826, 828, 830 and 832. In one embodiment, the first and second cardiac leads 802 and 804 have elongated bodies made of one or more materials suitable for implantation in a human body, where such materials are known in the art. Additionally, the electrodes are constructed of electrically conductive materials, such as platinum, platinum-iridium alloys, or other alloys as are known. The lead conductors are also constructed of electrically conductive materials such as MP35N, an alloy of nickel, chromium, cobalt, and molybdenum.

The implantable cardiac rhythm management device 800 includes control circuitry 840, where the control circuitry 840 is coupled to the electrodes 806, 808, 810, 812 and 814, from which at least a first cardiac signal is sensed, generates electrical energy pulses under predetermined conditions, and delivers electrical energy to electrodes positioned on the leads under the predetermined conditions.

In one embodiment, the control circuitry 840 is a programmable microprocessor-based system, with a microprocessor 842 and a memory circuit 844, which contains parameters for various pacing and sensing modes and stores data indicative of cardiac signals received by the control circuitry 840. The control circuitry 840 further includes a pulse circuit 846, a depolarization circuit 848 and a pulse adjustment circuit 850 which are coupled to each other and the microprocessor 842 and memory circuit 844 through bus 852. In one embodiment, the pulse circuit 846 is the pacing output circuit as previously described.

The implantable cardiac rhythm management device 800 further includes an evoked response sensing amplifier 860, where the amplifier 860 includes a first switch 854 and a second switch 856, under the control of microprocessor 842, to allow the amplifier 860 to be switched between various sensing configurations. In one embodiment, the amplifier 860 is used in conjunction with the pacing output circuit and autocapture protocols which are executed by the control circuitry 840 of the implantable cardiac rhythm management device 800. In one embodiment, the use of the evoked response sensing amplifier 860 allows for (1) sensing between either the first or second atrial electrode, 808 or 810, and the housing 820 or the indifferent electrode 822; (2) sensing between the first ventricular electrode 806 and the housing 820 or the indifferent electrode 822; (3) the first ventricular electrode 812 and the housing 820 or the indifferent electrode 822; and (4) for sensing between the first and second ventricular electrodes, 812 and 814.

In addition to the evoked response sensing amplifier 860, the implantable cardiac rhythm management device 800 further includes amplifier 862 and 864. In one embodiment, first and second ventricular electrodes, 812 and 814, are coupled to amplifier 862 to allow for a bipolar signal to be sensed between the electrodes. In addition, first and second atrial electrodes, 808 and 810, are coupled to amplifier 864 to allow for a bipolar signal to be sensed between the electrodes.

Generally, the pulse circuit 846 is coupled to at least one electrode and produces electrical pulses at the first value to be delivered to the at least one electrode in the first cardiac region, as previously described. In the embodiment shown in FIG. 8, the pulse circuit 846 is shown coupled to the electrodes 806, 808, 810, 812 and 814, where the pulse circuit 846 can generate electrical pulses at the first value to be delivered to any combination of the electrodes 806, 808, 810, 812 and 814 under the control of the control circuitry 840. Power to the implantable cardiac rhythm management device 800 is supplied by an electrochemical battery 860 that is housed within the device 800.

The output of each of the amplifiers 860, 862 and 864 is coupled to the depolarization circuit 848. As previously discussed, a first cardiac signal is sensed from which the occurrence of cardiac depolarizations is detected. In the present embodiment, the first cardiac signal is sensed from any combination of the first atrial electrode 808, the second atrial electrode 810 and the housing 820, such that the first cardiac region is an atrial region of the heart. In addition to detecting cardiac depolarizations which occur in the atrial region, the first cardiac signal will also contain indications of cardiac depolarizations which occur in the ventricles. From this, the depolarization circuit 848 can detect in the first cardiac signal any occurrence of cardiac depolarizations in the second cardiac region that occur in direct reaction to electrical pulses generated by the pulse circuit 846. As previously discussed, autocapture protocols are executed in the control circuitry 840 to monitor the capture of both atrium and ventricle chambers in response to electrical energy supplied to the one or more electrodes positioned in or around the coronary sinus vein.

As previously discussed, when a second cardiac region depolarizes as a direct reaction to electrical pulses delivered to a first cardiac region (e.g., pulses delivered to the stimulate the atrial region which instead, or additionally, stimulate the ventricular region) the present subject matter changes the first value of the electrical pulses. The embodiment shown in FIG. 8, the pulse adjustment circuit 850 modifies, or adjusts, the values of the electrical pulses when the depolarization circuit 848 detects the occurrence of a cardiac depolarization in the second cardiac region that occurs in direct reaction to an electrical pulse delivered in the first cardiac region. In one embodiment, the depolarization circuit 848 utilizes the autocapture protocols previously discussed to detect and identify the occurrence of cardiac depolarizations in the second cardiac region that occurs in direct reaction to electrical pulses delivered in the first cardiac region.

In one embodiment, when the depolarization circuit 848 detects the occurrence of the cardiac depolarization in the second cardiac region that occurs in direct reaction to the electrical pulse delivered to the at least one electrode in the first cardiac region, the pulse adjustment circuit 850 lowers the first value (e.g., voltage or pulse width) of the electrical pulses by the first amount, as previously discussed. In addition, the pulse adjustment circuit 850 sets the first value of the electrical pulses based on the previously discussed threshold test.

In one embodiment, the threshold test is conducted by the control circuitry 840, where the pulse circuit 846 delivers test pacing pulses at values over a first value range to at least one electrode. In one embodiment, the at least one electrode is either the first atrial electrode 808 or the second atrial electrode 810. As previously discussed, the first value range includes an initial step-down pacing pulse for which the depolarization circuit 848 detects a depolarization in the first cardiac region and the second cardiac region. During the step-down pacing pulse, the values of the test pacing pulses are reduced over the first value range at first intervals until the second cardiac region is no longer depolarized by the test pacing pulses. As previously discussed, this pacing pulse value is referred to as the second cardiac region pacing threshold value. The test pacing pulses are continued to be reduced by the control circuitry 740 until the first cardiac region is no longer depolarized by the test pacing pulses. As previously discussed, this pacing pulse value is referred to as the first cardiac region pacing threshold value. The pulse adjustment circuit 750 then sets the first value based on the first cardiac region pacing threshold value and the second cardiac region pacing threshold value in a manner as previously discussed. In a similar fashion, the control circuitry 840 controls the delivery of the step-up pacing pulses in the threshold test, as previously discussed, so as to set the first value based on the first cardiac region pacing threshold value and the second cardiac region pacing threshold value.

Electronic communication circuitry 864 is additionally coupled to the control circuitry 840 to allow communication with an external controller 866. In one embodiment, the electronic communication circuitry 864 includes a data receiver and a data transmitter to send and receive and transmit signals and cardiac data to and from an external programmer 866. In one embodiment, the data receiver and the data transmitter include a wire loop antenna to establish a radio frequency telemetric link, as is known in the art, to receive and transmit signals and data to and from the programmer unit 866.

This application is intended to cover any adaptations or variations of the present invention. It is manifestly intended that this invention be limited only by the claims and equivalents thereof.

What is claimed is:

1. A system, comprising:
   an electrode system which includes at least one electrode;
   control circuitry, where the control circuitry is coupled to the electrode system from which a first cardiac signal is sensed, and where the control circuitry includes:

a pulse circuit coupled to the electrode system, where the pulse circuit produces electrical pulses at a first value to be delivered to the electrode system in a first cardiac region;

a depolarization circuit coupled to the electrode system, where the depolarization circuit detects in the first cardiac signal an occurrence of cardiac depolarizations in a second cardiac region that occurs in direct reaction to electrical pulses generated by the pulse circuit; and a pulse adjustment circuit coupled to the pulse circuit, where the pulse adjustment circuit modifies the first value of the electrical pulses when the depolarization circuit detects the occurrence of a cardiac depolarization in the second cardiac region that occurs in direct reaction to an electrical pulse delivered to the at least one electrode in the first cardiac region.

2. The system of claim 1, where the pulse adjustment circuit lowers the first value of the electrical pulses by a first amount when the depolarization circuit detects the occurrence of the cardiac depolarization in the second cardiac region that occurs in direct reaction to the electrical pulse delivered to the electrode system in the first cardiac region.

3. The system of claim 2, where the first value of the electrical pulses is a first voltage value and the first amount the pulse adjustment circuit lowers the first voltage value is a percentage of the first voltage value.

4. The system of claim 2, where the first value of the electrical pulses is a first voltage value and the first amount the pulse adjustment circuit lowers the first voltage value is approximately 0.2 volts.

5. The system of claim 2, where the first value of the electrical pulses is a first energy value and the first amount the pulse adjustment circuit lowers the first energy value is a percentage of the first energy value.

6. The system of claim 1, where the pulse adjustment circuit sets the first value of the electrical pulses based on a threshold test.

7. The system of claim 6, where the threshold test is conducted by the control circuitry in which the pulse circuit delivers test pacing pulses at values over a first value range to the at least one electrode, where the first value range includes an initial hightest pacing pulse for which the depolarization circuit detects a depolarization in the first cardiac region and the second cardiac region, and where the values of the test pacing pulses are reduced over the first value range at first intervals until the second cardiac region is no longer depolarized by the test pacing pulses at a second cardiac region pacing threshold value and until the first cardiac region is no longer depolarized by the test pacing pulses at a first cardiac region pacing threshold value, where the pulse adjustment circuit sets the first value based on the first cardiac region pacing threshold value and the second cardiac region pacing threshold value.

8. The system of claim 7, where the pulse adjustment circuit sets the first value at a value midway between the first cardiac region pacing threshold value and the second cardiac region pacing threshold value.

9. The system of claim 8, where the pulse adjustment circuit adds a safety margin value to the first value midway between the first cardiac region pacing threshold value and the second cardiac region pacing threshold value.

10. The system of claim 7, where the first value range is approximately one (1) volt to ten (10) volts, and the initial high-test pacing pulse has a voltage value of approximately ten (10) volts.

11. The system of claim 6, where the threshold test is conducted by the control circuitry in which the pulse circuit delivers test pacing pulses at values over a first value range to the at least one electrode, where the first value range includes an initial low-test pacing pulse for which the depolarization circuit fails to detect a depolarization in the first cardiac region and the second cardiac region, and where the values of the test pacing pulses are increased over the first value range at first intervals until both the first cardiac region depolarize from the test pacing pulse and the second cardiac region does not depolarize from the test pacing pulse at a first cardiac region pacing threshold value and until the first cardiac region and the second cardiac region are depolarized by the test pacing pulse at a second cardiac region pacing threshold value, where the pulse adjustment circuit sets the first value based on the first cardiac region pacing threshold value and the second cardiac region pacing threshold value.

12. The system of claim 11, where the pulse adjustment circuit sets the first value at a value midway between the first cardiac region pacing threshold value and the second cardiac region pacing threshold value.

13. The system of claim 12, where the pulse adjustment circuit adds a safety margin value to the first value midway between the first cardiac region pacing threshold value and the second cardiac region pacing threshold value.

14. The system of claim 11, where the first value range is approximately one (1) volt to ten (10) volts, and the initial low-test pacing pulse has a voltage value of approximately one (1) volt.

15. The system of claim 1, where the electrode system includes a first cardiac lead and a second cardiac lead, where the first cardiac lead includes at least one electrode coupled to the control circuitry from which the first cardiac signal is sensed, and where the second cardiac lead includes at least one electrode coupled to the control circuitry from which the control circuitry detects a second cardiac signal and the depolarization circuit detects in the second cardiac signal cardiac depolarizations in the second cardiac region as a result of electrical pulses delivered to the first cardiac region.

16. A method, comprising:

delivering electrical pulses at a first value to a first cardiac region;

sensing at least one cardiac signal, where the cardiac signal includes indications of cardiac depolarizations;

detecting from the cardiac signal a cardiac depolarization from a second cardiac region which occurs in direct reaction to an electrical pulse delivered to the first cardiac region; and modifying the first value of the electrical pulses when the cardiac depolarization which occurs in direct reaction to the electrical pulse delivered to the first cardiac region is detected from the second cardiac region.

17. The method of claim 16, where delivering electrical pulses includes delivering electrical pulses at the first value to a supraventricular location, and detecting from the second cardiac region includes detecting from a ventricular cardiac region.

18. The method of claim 16, where modifying the first value of the electrical pulses includes lowering the first value of the electrical pulses by a first amount when the cardiac depolarization in the second cardiac region occurs in direct reaction to the electrical pulse delivered to the first cardiac region.

19. The method of claim 18, where lowering the first value includes lowering the first value of the electrical pulses by a first percentage of the first voltage value.

20. The method of claim 18, where lowering the first value includes lowering the first value of the electrical pulses by approximately two tenths (0.2) volts.

21. The method of claim 16, including conducting a threshold test, and setting the first value of the electrical pulses based on the threshold test.

22. The method of claim 21, where conducting the threshold test includes delivering test pacing pulses, including an initial high-test pacing pulse, at values over a first value range to the first cardiac region;

analyzing the cardiac signal for cardiac depolarizations from the first cardiac region and the second cardiac region which occur as a result of the initial high-test pacing pulse;

reducing the values of the test pacing pulses over the first value range until a second cardiac region pacing threshold value is reached where the second cardiac region is no longer depolarized and the first cardiac region is depolarized by the test pacing pulses;

continuing to reduce the values of the test pacing pulses over the first value range until a first cardiac region pacing threshold value is reached where both the first cardiac region and the second cardiac region are no longer depolarized by the test pacing pulses; and setting the first value based on the first cardiac region pacing threshold value and the second cardiac region pacing threshold value.

23. The method of claim 22, including setting the first value at a value midway between the first cardiac region pacing threshold value and the second cardiac region pacing threshold value.

24. The method of claim 23, including adding a safety margin value to the first value midway between the first cardiac region pacing threshold value and the second cardiac region pacing threshold value.

25. The method of claim 21, where conducting the threshold test includes delivering test pacing pulses, including an initial low-test pacing pulse, at values over a first value range to the first cardiac region;

analyzing the cardiac signal for cardiac depolarizations from the first cardiac region and the second cardiac region which occur as a result of the initial low-test pacing pulse;

increasing the values of the test pacing pulses over the first value range until a first cardiac region pacing threshold value is reached where the first cardiac region is depolarized and the second cardiac region is not depolarized by the test pacing pulses;

continuing to increase the values of the test pacing pulses over the first value range until a second cardiac region pacing threshold value is reached where both the first cardiac region and the second cardiac region are depolarized by the test pacing pulses; and setting the first value based on the first cardiac region pacing threshold value and the second cardiac region pacing threshold value.

26. The method of claim 25, including setting the first value at a value midway between the first cardiac region pacing threshold value and the second cardiac region pacing threshold value.

27. The method of claim 26, including adding a safety margin value to the first value midway between the first cardiac region pacing threshold value and the second cardiac region pacing threshold value.

28. A system, comprising:

means for delivering electrical pulses at a first value to a first cardiac region;

means for sensing at least one cardiac signal, where the cardiac signal includes indications of cardiac depolarizations;

means for detecting from the cardiac signal a cardiac depolarization from a second cardiac region which occurs in direct reaction to an electrical pulse delivered to the first cardiac region; and means for modifying the first value of the electrical pulses when the cardiac depolarization which occurs in direct reaction to the electrical pulse delivered to the first cardiac region is detected from the second cardiac region.

29. The system of claim 28, where the means for delivering electrical pulses includes means for delivering electrical pulses at the first value to a supraventricular location, and the means for detecting from the second cardiac region includes means for detecting from a ventricular cardiac region.

30. The system of claim 28, where the means for modifying the first value of the electrical pulses includes means for lowering the first value of the electrical pulses by a first amount when the cardiac depolarization in the second cardiac region occurs in direct reaction to the electrical pulse delivered to the first cardiac region.

31. The system of claim 28, including means for conducting a threshold test, and means for setting the first value of the electrical pulses based on the threshold test.

32. The system of claim 31, where the means for conducting the threshold test includes means for delivering test pacing pulses, including an initial high-test pacing pulse, at values over a first value range to the first cardiac region;

means for analyzing the cardiac signal for cardiac depolarizations from the first cardiac region and the second cardiac region which occur as a result of the initial high-test pacing pulse;

means for reducing the values of the test pacing pulses over the first value range until a second cardiac region pacing threshold value is reached where the second cardiac region is no longer depolarized and the first cardiac region is depolarized by the test pacing pulses;

means for continuing to reduce the values of the test pacing pulses over the first value range until a first cardiac region pacing threshold value is reached where both the first cardiac region and the second cardiac region are no longer depolarized by the test pacing pulses; and means for setting the first value based on the first cardiac region pacing threshold value and the second cardiac region pacing threshold value.

33. The system of claim 32, including means for setting the first value at a value midway between the first cardiac region pacing threshold value and the second cardiac region pacing threshold value.

34. The system of claim 33, including means for adding a safety margin value to the first value midway between the first cardiac region pacing threshold value and the second cardiac region pacing threshold value.

35. The system of claim 31, where the means for conducting the threshold test includes means for delivering test pacing pulses, including an initial low-test pacing pulse, at values over a first value range to the first cardiac region;

means for analyzing the cardiac signal for cardiac depolarizations from the first cardiac region and the second cardiac region which occur as a result of the initial low-test pacing pulse;

means for increasing the values of the test pacing pulses over the first value range until a first cardiac region pacing threshold value is reached where the first cardiac region is depolarized and the second cardiac region is not depolarized by the test pacing pulses;

means for continuing to increase the values of the test pacing pulses over the first value range until a second cardiac region pacing threshold value is reached where both the first cardiac region and the second cardiac region are depolarized by the test pacing pulses; and means for setting the first value based on the first cardiac region pacing threshold value and the second cardiac region pacing threshold value.

36. The system of claim 35, including means for setting the first value at a value midway between the first cardiac region pacing threshold value and the second cardiac region pacing threshold value.

37. The system of claim 36, including means for adding a safety margin value to the first value midway between the first cardiac region pacing threshold value and the second cardiac region pacing threshold value.

* * * * *